(12) United States Patent
Wu

(10) Patent No.: US 9,035,093 B2
(45) Date of Patent: May 19, 2015

(54) METHODS FOR PRODUCTION OF HIGH CONCENTRATION OF ARGININE BICARBONATE SOLUTION AT HIGH PRESSURE

(75) Inventor: Donghui Wu, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 268 days.

(21) Appl. No.: 13/515,829

(22) PCT Filed: Dec. 13, 2010

(86) PCT No.: PCT/US2010/059992
§ 371 (c)(1),
(2), (4) Date: Jun. 14, 2012

(87) PCT Pub. No.: WO2011/075422
PCT Pub. Date: Jun. 23, 2011

(65) Prior Publication Data
US 2012/0296117 A1 Nov. 22, 2012

Related U.S. Application Data

(60) Provisional application No. 61/287,846, filed on Dec. 18, 2009.

(51) Int. Cl.
*C07C 277/08* (2006.01)

(52) U.S. Cl.
CPC .................................... *C07C 277/08* (2013.01)

(58) Field of Classification Search
CPC ..................................................... C07C 277/08
See application file for complete search history.

(56) References Cited

U.S. PATENT DOCUMENTS

| | | | |
|---|---|---|---|
| 3,925,543 A | 12/1975 | Donohue | |
| 3,932,605 A | 1/1976 | Vit | |
| 3,932,608 A | 1/1976 | Anderson et al. | |
| 3,943,241 A | 3/1976 | Anderson et al. | |
| 3,988,434 A | 10/1976 | Schole et al. | |
| 4,011,309 A | 3/1977 | Lutz | |
| 4,022,880 A | 5/1977 | Vinson et al. | |
| 4,025,616 A | 5/1977 | Haefele | |
| 4,042,680 A | 8/1977 | Muhler et al. | |
| 4,064,138 A | 12/1977 | Saari et al. | |
| 4,100,269 A | 7/1978 | Pader | |
| 4,108,979 A | 8/1978 | Muhler et al. | |
| 4,108,981 A | 8/1978 | Muhler et al. | |
| 4,146,607 A | 3/1979 | Ritchey | |
| 4,154,813 A | 5/1979 | Kleinberg | |
| 4,160,821 A | 7/1979 | Sipos | |
| 4,213,961 A | 7/1980 | Curtis et al. | |
| 4,225,579 A | 9/1980 | Kleinberg | |
| 4,259,316 A | 3/1981 | Nakashima et al. | |
| 4,269,822 A | 5/1981 | Pellico et al. | |
| 4,305,928 A | 12/1981 | Harvey | |
| 4,335,102 A | 6/1982 | Nakashima et al. | |
| 4,339,432 A | 7/1982 | Ritchey et al. | |
| RE31,181 E | 3/1983 | Kleinberg | |
| 4,466,954 A | 8/1984 | Ichikawa et al. | |
| 4,528,181 A | 7/1985 | Morton et al. | |
| 4,532,124 A | 7/1985 | Pearce | |
| 4,538,990 A | 9/1985 | Pashley | |
| 4,645,662 A | 2/1987 | Nakashima et al. | |
| 4,656,031 A | 4/1987 | Lane et al. | |
| 4,725,576 A | 2/1988 | Pollock et al. | |
| 4,885,155 A | 12/1989 | Parran, Jr. et al. | |
| 4,919,910 A | 4/1990 | Kurtz et al. | |
| 4,997,640 A | 3/1991 | Bird et al. | |
| 5,096,700 A | 3/1992 | Seibel et al. | |
| 5,286,480 A | 2/1994 | Boggs et al. | |
| 5,334,617 A | 8/1994 | Ulrich et al. | |
| 5,370,865 A | 12/1994 | Yamagishi et al. | |
| 5,639,795 A | 6/1997 | Friedman et al. | |
| 5,747,004 A | 5/1998 | Giani et al. | |
| 5,762,911 A | 6/1998 | Kleinberg et al. | |
| 5,906,811 A | 5/1999 | Hersh | |
| 5,922,346 A | 7/1999 | Hersh | |
| 5,997,301 A | 12/1999 | Linden | |
| 6,217,851 B1 | 4/2001 | Kleinberg et al. | |
| 6,436,370 B1 | 8/2002 | Kleinberg et al. | |

(Continued)

FOREIGN PATENT DOCUMENTS

| EP | 1135110 | 9/2001 |
|---|---|---|
| EP | 1736135 | 12/2006 |

(Continued)

OTHER PUBLICATIONS

US 5,989,525, 11/1999, Kleinberg et al. (withdrawn).

(Continued)

*Primary Examiner* — Paul A Zucker
(74) *Attorney, Agent, or Firm* — Rena Patel

(57) ABSTRACT

Methods of producing arginine bicarbonate solutions in very high concentrations including reacting an arginine slurry containing a first portion of arginine with a source of carbon dioxide gas at elevated pressure and temperature, adding subsequent portions of arginine to the resulting solution and further reacting with compressed carbon dioxide until a final solution containing in excess of 50% by weight are provided which include preparing an arginine solution by subjecting an arginine water slurry to elevated pressure and temperature and reacting the arginine solution with a source of carbon dioxide gas to form a solution comprising arginine and bicarbonate anion and recovering arginine bicarbonate from the solution.

18 Claims, 1 Drawing Sheet

(56) References Cited

U.S. PATENT DOCUMENTS

| | | | |
|---|---|---|---|
| 6,488,961 | B1 | 12/2002 | Robinson et al. |
| 6,524,558 | B2 | 2/2003 | Kleinberg et al. |
| 6,558,654 | B2 | 5/2003 | McLaughlin |
| 6,805,883 | B2 | 10/2004 | Chevaux et al. |
| 6,890,497 | B2 | 5/2005 | Rau et al. |
| 8,399,704 | B2 * | 3/2013 | Kohli et al. .................. 562/560 |
| 2002/0081360 | A1 | 6/2002 | Burgard et al. |
| 2003/0215513 | A1 | 11/2003 | Fyhr et al. |
| 2007/0154863 | A1 | 7/2007 | Cai et al. |
| 2009/0202456 | A1 | 8/2009 | Prencipe et al. |

FOREIGN PATENT DOCUMENTS

| | | |
|---|---|---|
| FR | 2547501 A1 * | 12/1984 |
| WO | WO 96/41617 | 12/1996 |
| WO | WO 97/32565 | 9/1997 |
| WO | WO 00/78270 | 12/2000 |
| WO | WO 2007/008908 | 1/2007 |
| WO | WO 2009/099451 | 8/2009 |
| WO | WO 2009/100267 | 8/2009 |
| WO | WO 2009/100267 A1 * | 8/2009 |
| WO | WO 2009/100278 | 8/2009 |

OTHER PUBLICATIONS

Acevedo et al., 2005, "The Inhibitory Effect of an Arginine Bicarbonate/Calcium Carbonate (CaviStat)-Containing Dentifrice on the Development of Dental Caries in Venezuelan School Children," J. Clinical Dentistry 16(3):63-70.

AminoScience L-Arginine recovered from http://www.ajinomoto.co.jp/kfb/amino/e_aminoscience/bc/amino_02.html on Mar. 30, 2012.

Chatterjee et al., 2005, "Bacterial Acidification and CaviStat Alkalinization of Occlusal Fissure pH," Abstract, 83rd Session of the American Association for Dental Research, Mar. 9-12, 2005, Baltimore, MD.

International Search Report and Written Opinion in International Application No. PCT/US09/033293, mailed Jun. 24, 2009.

International Search Report and Written Opinion in International Application No. PCT/US10/059992, mailed May 18, 2011.

International Search Report and Written Opinion in International Application No. PCT/US10/060266, mailed Mar. 14, 2011.

Kleinberg, 1999, "A New Saliva-Based Anticaries Composition," Dentistry Today 18(2):1-6.

Kleinberg, 2002, "A Mixed-Bacteria Ecological Approach to Understanding the Role of the Oral Bacteria in Dental Caries Causation: An Alternative to *Streptococcus mutans* and the Specific-Plaque Hypothesis," Critical Reviews in Oral Biological Medicine 13(2):108-125.

Machado et al., 2007, "CaviStat confetion Inhibition of Caries in Posterior Teeth," Abstract, 83rd Session of the American Association for Dental Research, Mar. 21-24, 2007, New Orleans, LA.

Packaging with Ingredient List for DenClude® (launched Dec. 2004).

Packaging with Ingredient List for ProClude® (launched Jul. 2002).

Written Opinion in International Application No. PCT/US10/059992, mailed Nov. 16, 2011.

* cited by examiner

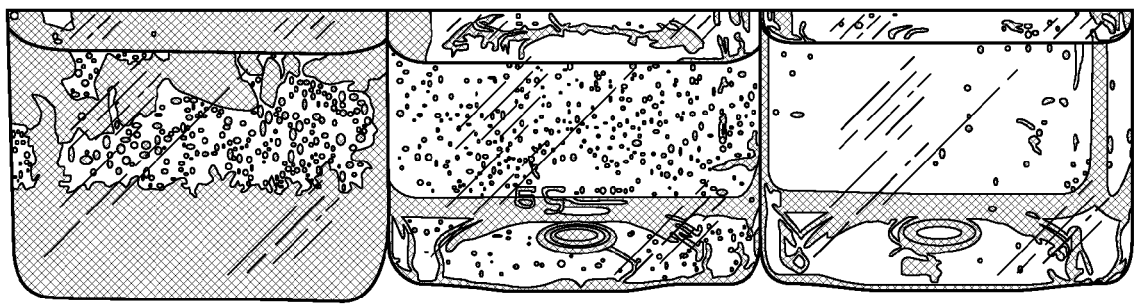

METHODS FOR PRODUCTION OF HIGH CONCENTRATION OF ARGININE BICARBONATE SOLUTION AT HIGH PRESSURE

CROSS REFERENCE TO RELATED APPLICATIONS

This application is a national stage entry under 35 U.S.C. §371 of International Patent Application No. PCT/US2010/059992, filed 13 Dec. 2010, which claims priority to U.S. Provisional Patent Application Ser. No. 61/287,846, filed on 18 Dec. 2009, which is incorporated herein by reference.

BACKGROUND

Arginine bicarbonate has use in various industrial applications, including use in personal care compositions, such as oral care compositions. For example, U.S. Pat. No. 6,524,558 describes the use of arginine bicarbonate and calcium carbonate for preventing or treating dental hypersensitivity. As the industrial requirements for arginine bicarbonate increase, so will the need for improved processes and methods for its manufacture.

PCT published application WO2009/100267, the contents of which are incorporated herein in their entirety as if set forth in full, describes methods of production of arginine bicarbonate.

Arginine bicarbonate may be produced by bubbling carbon dioxide gas through a saturated arginine aqueous solution at room temperature and pressure. U.S. Pat. No. 6,217,851 describes preparing arginine bicarbonate from arginine hydroxide by bubbling carbon dioxide or by adding dry ice in excess into a solution of arginine free base. However, the efficiency of the existing process needs to be improved. The existing process is slow, requiring 24 to 48 hours to complete the reaction. Carbon dioxide has very limited solubility in water, and releasing the gas into the solution produces a maximum concentration of $1.2 \times 10^{-5}$ M at room temperature and its natural partial pressure ($3.5 \times 10^{-4}$ atmosphere). The solubility of arginine in water is only 15% weight/weight at room temperature. Producing a concentrated arginine bicarbonate solution (e.g., 40%) requires the continual addition of arginine to the solution, thereby increasing production time and requiring constant monitoring of the reaction. Thus, there is a need to improve methods to manufacture arginine bicarbonate.

SUMMARY

Methods for manufacturing arginine bicarbonate. These methods represent a significant improvement over existing techniques, as a highly concentrated solution of arginine and bicarbonate anions in excess of 50%, and in certain embodiments in excess of 75% w/w may be produced in as little as 10 to 20 minutes (vs. 24-48 hours to produce far lower concentrations of arginine bicarbonate using the prior art methods), followed by faster and easier recovery processes of arginine bicarbonate salt from the solution.

In one embodiment, a method of producing arginine bicarbonate including contacting carbon dioxide having a pressure of at least 34474 Pa (5 psi) with a starting slurry containing arginine at a temperature of at least 30° C.; adding arginine to the contacted slurry to increase the arginine content to greater than 65% by weight; contacting the increased arginine slurry with carbon dioxide until the slurry has a pH below 9; and recovering arginine bicarbonate from the slurry.

In another embodiment, a process for producing arginine bicarbonate is disclosed that includes contacting an arginine water slurry with carbon dioxide having a pressure greater than 551580 Pa (80 psi); heating the arginine water slurry to a temperature within the range of from 60° C. to 80° C.; adding arginine to the slurry until arginine comprises 65% by weight; contacting carbon dioxide with the increased arginine slurry until the slurry has a pH below 9; cooling the slurry to a temperature of 25° C.

In yet another aspect, a method of producing arginine bicarbonate including subjecting an arginine water slurry to elevated pressure and temperature; contacting the slurry with carbon dioxide to form a slurry comprising arginine and bicarbonate in excess of 65% by weight of arginine; and recovering arginine bicarbonate from the slurry.

BRIEF DESCRIPTION OF THE DRAWINGS

Certain embodiments are described in the examples that follow and illustrated in the figures appended hereto.

FIG. 1 illustrates reaction products from various conditions in clear plastic bottles, wherein arginine was added to a Parr reactor in: right (sample #1)—single step; middle (sample #2)—two steps; and left (sample #3)—three steps.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% may include 9.5% or 10.5%, given the degree of error in measurement that will be appreciated and understood by those having ordinary skill in the art. The method involves a surprisingly simple reaction to produce a high concentration of arginine bicarbonate salt by reacting a source of gaseous carbon dioxide and an arginine slurry under elevated temperature and low pressure to form an arginine and bicarbonate anion solution, wherein the salt is then recovered from solution. The initial reaction is faster than existing methods, 90 minutes vs. over 24 hours, and yields a more concentrated solution of arginine and bicarbonate anion (above 50%, and in certain embodiments 70% or above, vs. 40%).

The method is directed to a surprisingly simple reaction to produce a high concentration of arginine bicarbonate salt solution by reacting a source of gaseous carbon dioxide and an arginine slurry under elevated temperature and pressure to form an arginine and bicarbonate anion solution, wherein the salt is then recovered from solution. The initial reaction is faster than existing methods, from 10 to 20 minutes vs. over 24 hours, and yields a more concentrated solution of arginine and bicarbonate anion (in certain embodiments in excess of 75% vs. 40%).

In one embodiment, a method of producing arginine bicarbonate including contacting carbon dioxide having a pressure of least 34474 Pa (5 psi) with a starting slurry containing arginine at a temperature of at least 30° C.; adding arginine to the contacted slurry to increase the arginine content to greater than 65% by weight; contacting the increased arginine slurry with carbon dioxide until the slurry has a pH below 9; and recovering arginine bicarbonate from the slurry.

In another embodiment, a process for producing arginine bicarbonate is disclosed that includes contacting an arginine water slurry with carbon dioxide having a pressure greater than 551580 Pa (80 psi); heating the arginine water slurry to a temperature within the range of from 60° C. to 80° C.; adding arginine to the slurry until arginine comprises 65% by weight; contacting carbon dioxide with the increased arginine slurry until the slurry has a pH below 9; cooling the slurry to a temperature of 25° C.

In yet another aspect, a method of producing arginine bicarbonate including subjecting an arginine water slurry to elevated pressure and temperature; contacting the slurry with carbon dioxide to form a slurry comprising arginine and bicarbonate in excess of 65% by weight of arginine; and recovering arginine bicarbonate from the slurry.

In one embodiment, the arginine slurry includes arginine and a solvent, in certain embodiments water, wherein the subsequent portions of arginine are added stepwise or continuously in the form of a free base or salt. In an embodiment, the arginine water slurry is in a ratio of 50:50 by weight with respect to the first portion of arginine. Subsequent portions of arginine may be added until the ratio of arginine to water is in excess of 1.8:1, in certain embodiments in excess of 1.9:1, in certain embodiments in excess of 2.0:1, and in certain embodiments in excess of 2.5:1.

The arginine used in the methods in certain embodiments is selected from L-arginine, D-arginine, or a mixture thereof. The arginine also can be provided by arginine hydroxide, arginine hydrochloride, or a mixture thereof.

In the methods, the carbon dioxide can be provided to the reaction as a gas under pressure from 34474 Pa (5 psi) to 1723689 Pa (250 psi), in certain embodiments from in excess of 275790 Pa (40 psi) to in excess of 551580 Pa (80 psi), and in certain embodiments at 551580 Pa (80 psi).

In another embodiment, the bicarbonate ion can be generated by providing sodium bicarbonate to the slurry. In another embodiment, the arginine slurry and carbon dioxide can be maintained under elevated temperature and pressure for 10 minutes to 20 minutes. Those having ordinary skill in the art will appreciate that while the reaction can proceed for as little as 10-20 minutes for lab or pilot scale production of arginine bicarbonate, commercial quantity scale production of arginine bicarbonate typically will take longer, up to 5 hours. The arginine slurry and carbon dioxide therefore can be maintained under elevated temperature and pressure for 10 minutes to 5 hours, in certain embodiments from 10 minutes to 4 hours, and in certain embodiments from 10 minutes to 2-4 hours, for commercial scale production.

In another aspect, the arginine slurry can first be heated to a temperature within the range of from 30° C. to 80° C., in certain embodiments from 50° C. to 80° C. for the duration of the reaction, then cooled to a temperature within the range of from 0° C. to 40° C. after completion of the reaction, in certain embodiments from 0° C. to 25° C. The arginine slurry in certain embodiments has a pH of 10 to 14. By utilizing the methods, the arginine bicarbonate solution has a pH of from 7 to 10, in certain embodiments a pH of 7.5 to 8.5 (or 7.0 to 9.0). That is, the reaction is believed to be substantially completed when the pH of the resulting solution containing the arginine bicarbonate is below 9.0.

The present method in certain embodiments begins with the formation of an arginine slurry comprising arginine and a solvent, in certain embodiments water. As arginine free base is only slightly soluble at water at room temperature, the addition of arginine to water forms a slurry, wherein a majority of the arginine is insoluble. Any form of arginine may be utilized to form the slurry, e.g., arginine free base (in D or L form, usually L-form), or an arginine salt. It is understood that various arginine salts, e.g., hydrochloride, and pharmaceutically acceptable salts, may be substantially more soluble in water than arginine free base, and this may allow for the production of more concentrated arginine and bicarbonate anion solution. Thus, salts may be used or mixtures of free base and salts may be used in combination to form the slurry.

The slurry in certain embodiments is produced by the addition of 10% to 90% weight of arginine to the solvent, e.g., 20% to 80%, 30% to 70%, 40% to 60%. The slurry may then be agitated to create a homogenous mixture. The initial pH of the slurry is generally 12 for arginine free base, e.g., 10 to 13.

In one embodiment, the arginine water slurry is in a ratio of 50:50 w/w. In one embodiment, the slurry may be heated to 30° C. to 80° C., e.g., to 40° C., to 50° C., to 55° C., to 60° C., to 65° C., or to 70° C. to increase the solubility of the arginine. In one embodiment, the arginine water slurry is first heated from 60° C. to 80° C.

The reaction between carbon dioxide in gaseous form and water is well known in the art, wherein carbonic acid is initially formed, and disassociates into bicarbonate and hydrogen ions. The bicarbonate then further disassociates into carbonate and an additional hydrogen ion. In methods, carbon dioxide is added to the arginine slurry in a pressurized vessel to form bicarbonate anions, resulting in a protonated arginine cation and bicarbonate anion solution.

The equilibrium of carbon dioxide/carbonic acid and arginine is set forth in Reactions 1 and 2 below, respectively. When carbon dioxide is purged in to water, it will form carbonic acid and bicarbonate, and then react with very basic arginine molecule to form arginine-bicarbonate, as shown in Reaction 3.

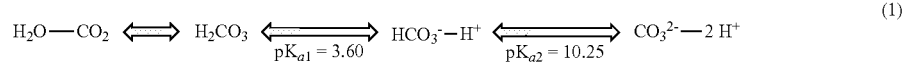

$$H_2O\text{---}CO_2 \rightleftharpoons H_2CO_3 \underset{pK_{a1} = 3.60}{\rightleftharpoons} HCO_3^-\text{---}H^+ \underset{pK_{a2} = 10.25}{\rightleftharpoons} CO_3^{2-}\text{---}2H^+ \quad (1)$$

-continued

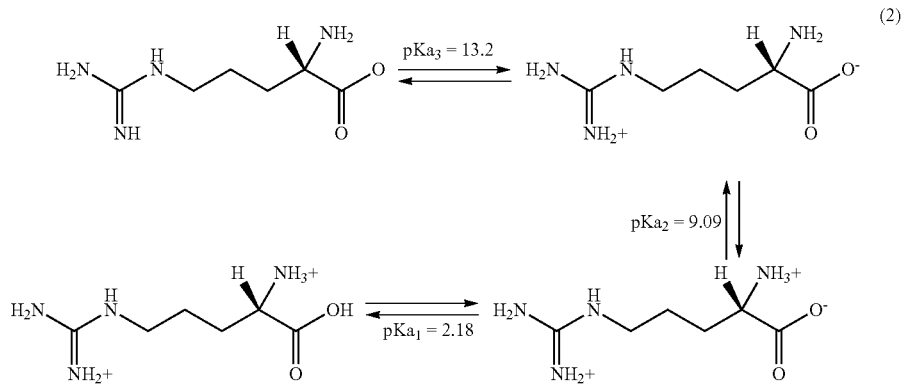

The solubility of carbon dioxide into the slurry may be increased by decreasing the temperature of the solution; however, this decreases the solubility of the arginine. Thus, it is desired that a careful balance be maintained between solubility of both components. Thus, in one embodiment, the pressurized vessel may be temperature controlled. One method of increasing the solubility of the carbon dioxide into the slurry is to provide the carbon dioxide at a lower temperature than that of a slurry, for example, by introducing carbon dioxide as dry ice, or a cooled gas. In certain embodiments, carbon dioxide gas is used in the present reaction. Additionally, direct cooling of the slurry may be significant.

The solubility of carbon dioxide into the slurry may be increased by increasing the partial pressure of the carbon dioxide in the reaction vessel. Thus, the reaction between the carbon dioxide and the arginine slurry may occur at 34474 Pa (5 psi) to 1034214 Pa (150 psi), e.g., to 344738 Pa (50 psi), to 413685 Pa (60 psi), to 482633 Pa (70 psi), to 551580 Pa (80 psi), to 620528 Pa (90 psi), to 689476 Pa (100 psi), to 758423 Pa (110 psi), to 827371 Pa (120 psi), or to 965266 Pa (140 psi).

In the reaction between arginine slurry and gaseous carbon dioxide, the pressure typically is maintained within a range of from 137895 Pa (20 psi) to 551580 Pa (80 psi) in order to take advantage of the higher solubility of $CO_2$ gas in water at higher partial $CO_2$ pressure. In one embodiment, a high pressure reaction vessel such as a Parr instrument model 425HC T316 can be used.

In an embodiment, arginine powder is added to a reactor containing water in a 50:50 arginine water ratio and reacted with carbon dioxide gas compressed at pressure in excess of 134474 Pa (5 psi) and a temperature greater than 50° C. to 75° C. until an almost clear solution is formed. Subsequent portions of powder arginine are added to the resulting clear solution until the ratio of arginine to water is 1.9:1. Depending on the completion of the reaction, in certain embodiments when no solid arginine remains, the arginine bicarbonate solution is clear and colorless, and the pH is less than 9.0, then additional carbon dioxide may be added to the reaction vessel. By adding arginine powder to the resulting arginine solution present in the reaction in a stepwise manner, an arginine bicarbonate solution having a final concentration in excess of 50%, in certain embodiments in excess of 60%, in certain embodiments, in excess of 65%, in certain embodiments in excess of 70%, and in certain embodiments in excess of 75% (even as high as 76%) arginine bicarbonate can be obtained.

The reaction between the arginine slurry and carbon dioxide may be allowed to proceed for 10 to 20 minutes. When carbon dioxide is reacted with a solution of arginine, the reaction time required to obtain an arginine bicarbonate solution having a final concentration in excess of 50% arginine bicarbonate is also from 10 minutes to 20 minutes. The completion of the reaction may be gauged by monitoring the presence of undissolved arginine in the slurry, as arginine in the presence of bicarbonate anions are highly soluble compared to the arginine itself. Another method to monitor the reaction is to measure the pH of the solution in the reaction vessel directly, or sample the solution and measure its pH in an open container at room temperature. In certain embodiments, the pH can be measured as a means of assessing whether the reaction has completed, and, in certain embodiments, the pH be below 9.0 before completion of the reaction.

Following the production of the arginine bicarbonate solution, the arginine bicarbonate salt may be recovered by any means known by those of skill in the art. In one embodiment, the solvent is evaporated, e.g., by heating, spray drying, or freeze drying. In another embodiment, the salt is precipitated from solution by the addition of alcohol.

The present methods may be utilized to produce arginine bicarbonate in single batches, or may be used in a continuous process, such as in continuous stirred tank reactors, fluidized bed reactors, and plug flow reactors. Those skilled in the art will be capable of carrying out the methods described herein in single batch or continuous processes, using the guidelines provided herein.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

SPECIFIC EMBODIMENTS

Example 1

A slurry of pH 12 containing 50% L-arginine by weight and 50% water by weight is prepared by mixing 85 g of L-arginine with 85 g of water at room temperature. The slurry is heated to 55° C. under gentle agitation. Approximately 50% of the L-arginine is determined to be dissolved by visual observation.

Example 2

25 grams of dry ice particles are added to the slurry produced in EXAMPLE 1, and the mixture is transferred to a pressurized vessel. The dry ice is allowed to sublime in order to purge atmospheric air from the vessel, and then the vessel is sealed. Pressure in the vessel is allowed to increase to 551580 Pa (80 psi), and the solution is maintained under pressure for 3 minutes. When the vessel is opened, a small amount of unreacted arginine is observed at the bottom of the vessel.

Example 3

The solution of EXAMPLE 2 is stirred with a spatula to make a suspension. 10 grams of dry ice is added to the vessel, and the vessel is sealed. The pressure is allowed to increase to, and maintained at 620528 Pa (90 psi). The vessel is opened after 3 minutes, and a thick clear colorless solution was observed without precipitation. The solution is dropped to 12° C. producing an arginine bicarbonate solution of 60% concentration, having a final pH of 8.8. Arginine bicarbonate salt is recovered by freeze drying.

Example 4

Arginine water slurry and compressed $CO_2$ gas are reacted in a series of reactions performed in a 300 ml high pressure reactor from Parr Instruments (425HC 300 ml cylinder, commercially available from Parr Instruments, Moline, Ill.) with a $CO_2$ injection port and fittings. The reactor included a port with an L-shaped stainless steel tube wherein the tube went to the bottom of the reactor. This port served as the $CO_2$ inlet port, which allowed $CO_2$ gas to be blown directly into the reactants, so that it also served as the mixer/agitator. The reactor also included a T-connector that connected the reactor to a purge valve and emergency relief valve at the top for safety. The reactor body sat inside a thermo-bath, so that the reaction temperature could be precisely controlled.

The thermo-bath is allowed to reach its preset temperature. Powder L-arginine is mixed with deionized water in the high pressure reactor by a spatula. The reactor is capped, its purge valve is kept open, and then the reactor is placed into the thermo-bath so that the reactants could reach the desired temperature. After thermo-equilibrium is reached in the thermo-bath, the compressed $CO_2$ gas is introduced into the reactor. The purge valve is kept partially open so that there is constant flow of $CO_2$ gas through the reactor to provide agitation. The gas pressure is regulated using a dual stage regulator on the $CO_2$ tank, and the pressure reading is taken from the gauge on the regulator. Since the purge valve is always open, the pressure inside the reactor is slightly lower than the value shown on the regulator gauge. Each reaction is allowed to progress for a constant time period, then the $CO_2$ gas supply is turned off. The reactor is opened immediately, and the contents in the reactor are transferred into a plastic container. The plastic container is capped tightly and submerged into a tap water bath at room temperature to cool it down. The pH of the final solution at room temperature is measured with a standard glass electrode pH meter.

40 grams of powder L-arginine of Ajinomoto C-grade are mixed with 40 grams of deionized water in a 1:1 weight ratio for reaction. After reaction, 60% (w/w) arginine bicarbonate aqueous solution was obtained. The reaction temperatures are 45, 60, and 75° C., and the pressures are 68948 Pa (10 psi), 137895 Pa (20 psi), 275790 Pa (40 psi), 413685 Pa (60 psi), and 551580 Pa (80 psi) as shown on the gauge on the $CO_2$ tank regulator. The thermo-equilibrium time is for 5 minutes and the reaction time is for 10 minutes. Detailed compositions and conditions utilized for the reactions performed at high pressure and temperature are listed in Table 1.

TABLE 1

Compositions, reaction conditions and final pH

| Arginine Weight (g) | Water Weight (g) | Temperature (° C.) | Pressure (Pa (psi)) | pH | Comments |
|---|---|---|---|---|---|
| 44.186 | 43.856 | 75.0 | 551580 (80) | 7.43 | |
| 42.216 | 43.254 | 75.0 | 413685 (60) | 7.63 | |
| 42.246 | 42.182 | 75.0 | 275790 (40) | 8.13 | |
| 42.433 | 42.594 | 75.0 | 137895 (20) | 8.36 | |
| 43.465 | 43.457 | 75.0 | 82737 (12) | 8.63 | |
| 41.295 | 42.229 | 60.0 | 551580 (80) | 7.55 | |
| 40.701 | 40.269 | 60.0 | 413685 (60) | 8.10 | |
| 40.652 | 40.633 | 60.0 | 275790 (40) | 8.29 | |
| 40.680 | 40.750 | 60.0 | 137895 (20) | 8.63 | very small amount of un-reacted arginine solid was observed |
| 41.977 | 41.354 | 60.0 | 68948 (10) | 8.78 | small amount of un-reacted arginine solid was observed |
| 40.887 | 40.989 | 45.0 | 551580 (80) | 8.20 | |
| 40.348 | 40.856 | 45.0 | 413685 (60) | 8.41 | |
| 41.226 | 41.993 | 45.0 | 275790 (40) | 8.64 | small amount of un-reacted arginine solid was observed |
| 40.082 | 40.397 | 45.0 | 137895 (20) | 9.11 | un-reacted arginine solid was observed |
| 40.657 | 40.116 | 45.0 | 68948 (10) | 9.31 | significant amount of un-reacted arginine solid was observed |

The reactions listed in Table 1 are allowed to run at similar conditions for 10 minutes, varying one parameter at a time. Then, the final pH values are used to determine the efficiencies or completeness of various reaction conditions. It is desirable to use final pH as the indicator, since the pH of aqueous solution under $CO_2$ gas at different pressures would not be an accurate indicator and in-line turbidity measurement also presented complications with gas bubbles.

The final pH values are plotted against $CO_2$ gas pressure, and data from reactions at three temperatures (75, 60, and 45) are determined and set out in Table 1. With reference to Table 1, it is readily apparent that $CO_2$ pressure had the strongest impact on the reaction rate, namely, the higher the pressure, the faster the reaction, and the lower the final pH. For example, at 75° C. and 551580 Pa (80 psi), the final pH dropped below 7.5 within 10 minutes of reaction from an initial value that is above 12.0. The data displayed in Table 1 also show that a higher temperature improves the reaction rate, but its effect is not as dramatic as that of high pressure, especially when the temperature is above 60° C.

It also is noted that a higher pressure produced more agitation, since the $CO_2$ gas stream is used as agitator in the reactor. Without being bound by theory, it is believed that a faster reaction rate at higher pressures is also due to more vigorous agitation. This is demonstrated by one reaction in which the purge valve was closed during the reaction, and the final pH was significantly higher than the pH of a reaction run under the same conditions, except the purge valve was partially open to allow constant gas flow for agitation. This experiment also indicated that good agitation may be important for a fast reaction.

After the reaction was completed, when the reactor was cooled down in ice water bath while maintaining an elevated $CO_2$ pressure, the final pH was significantly lower than was obtained when the reaction under the same condition omitted a final cool down, namely, the reactor was opened to air at the reaction temperature. This may have been due to the fact that $CO_2$ has higher solubility in water at lower temperature.

Example 5

In this example, three arginine bicarbonate samples are prepared, in which the arginine is added all at once in sample 1 and stepwise in samples 2 and 3. In all three samples, the reaction temperature is 75° C. and the pressure is maintained at 551580 Pa (80 psi) for a total time of 12 minutes. In Sample 1, arginine bicarbonate is prepared by adding to the reactor vessel an arginine water slurry in a ratio in excess of 1.8:1 of arginine to water in one step. It was found that the slurry was more like "damp powder" in solid form. It was observed through the bottom of the Parr reactor that all the "damp powder" was pushed to one side of the reactor since all the water was absorbed by arginine powder, and no free water was left. As expected, this starting material did not work very well for the reaction, even at 75° C. and 551580 Pa (80 psi). After a reaction time of 12 minutes, a large amount of un-reacted and un-dissolved arginine in solid form was observed, as shown in the bottle at left of FIG. 1. Table 2, below, lists the conditions and parameters for this reaction under Sample 1.

To increase the reaction rate, in a second sample as shown in Table 2, the above procedure is modified by performing multiple additions of arginine powder, at similar conditions as previously described. The majority of arginine powder, in excess of 80% is added to the Parr reactor and mixed with water first to obtain a slurry instead of "damp powder," as in Sample 1. In Sample 2, the ratio of the arginine to water in the slurry is 1.5:1. The reactor is closed and thermo-equilibrated for 5 minutes. $CO_2$ gas compressed at 551580 Pa (80 psi) is introduced into the reactor for 5 minutes to allow the arginine slurry to react with $CO_2$. Then, the reactor is opened immediately and the rest of arginine powder, less than 20% of total arginine, is added, and mixed with the clear solution inside the reactor by a spatula. The reactor is closed and compressed $CO_2$ gas is introduced into the reactor again. The reaction is allowed to run for another 7 minutes for a total of 12 minutes reaction time. An almost clear solution with barely any visible amount of solid arginine was obtained, as shown in the clear plastic bottle in the middle of FIG. 1.

In another example of multiple stepwise additions reaction, the arginine powder is added in three portions, at the beginning of the reaction and then at 3, and 6 minutes intervals thereafter, as shown in Sample 3 of Table 2. A completely clear solution was obtained with no solid arginine powder left as shown in the right clear plastic bottle of FIG. 1. The detailed condition and parameters of all reactions are listed in Table 2, below.

TABLE 2

Reaction conditions and compositions for samples 1 to 3

| Sample# | Arginine Weight $1^{st}$ Addition & Reaction Time | Water Weight | Arginine Weight $2^{nd}$ Addition & Reaction Time | Arginine Weight $3^{rd}$ Addition & Reaction Time |
|---|---|---|---|---|
| 1 | 54.002 g, 12 min | 30.841 g | 0 g | 0 g |
| 2 | 44.106 g, 5 min | 30.124 g | 10.030 g, 7 min | 0 g |
| 3 | 30.073 g, 3 min | 30.655 g | 12.151 g, 3 min | 11.837 g, 6 min |

Without being bound by any theory of operation, it is believed that at high concentrations the solution of arginine is very viscous, and high viscosity prevents a fast reaction from occurring. If the reaction starts from lower concentration, most arginine will be able to react quickly at low concentration and therefore low viscosity, and only a small amount of arginine need to be reacted at high concentration and high viscosity at a slower rate.

This example demonstrated that the reaction could proceed to completion faster when arginine powder is added to the reactor gradually in multiple steps. In one embodiment, the arginine powder could be added into the reactor continuously, to further improve the reaction rate. In this way, added arginine could dissolve and react immediately without remaining in a solid form for a prolonged period of time. As a result of gradually adding arginine into the reactor rather than dispensing all the arginine at once, an aqueous solution is produced efficiently and very quickly in 10 minutes.

These experimental results indicate that multiple or continuous addition of arginine into the reactor contributed to a fast, complete and efficient reaction. Other relevant factors included: (i) high partial pressure of $CO_2$ gas in excess of 134474 Pa (5 psi); (ii) high temperature in excess of 50° C. for the reactants except at the final stage of the reaction; (iii) the temperature should be less than 20° C. for the reactants at the final stage of the reaction; and (iv) ample agitation.

What is claimed is:

1. A method of producing arginine bicarbonate comprising:
   contacting carbon dioxide having a pressure of least 34474 Pa (5 psi) with a starting slurry containing arginine at a temperature of at least 30° C.;
   adding arginine to the contacted slurry to increase the arginine content to greater than 65% by weight;
   contacting the slurry with arginine content greater than 65% by weight with carbon dioxide until the slurry has a pH below 9; and
   recovering arginine bicarbonate from the slurry.

2. The method of claim 1 comprising additionally adding the arginine to the contacted slurry continuously in the form of a free base or a salt.

3. The method of claim 1, wherein the slurry comprises water.

4. The method of claim 1, wherein the starting slurry comprises 50% arginine by weight.

5. The method claim 1, wherein arginine is selected from L-arginine, D-arginine, or a mixture thereof.

6. The method of claim 1, wherein arginine is selected from arginine hydroxide, arginine hydrochloride, or a mixture thereof.

7. The method of claim 1, wherein the pressure of the carbon dioxide is from 137895 Pa (20 psi) to 1723689 Pa (250 psi).

8. The method of claim 1, wherein pressure of the carbon dioxide is in excess of 275790 Pa (40 psi).

9. The method of claim 1, wherein the temperature of the slurry is above 25° C. and the pressure of the slurry is above atmospheric pressure for 10 minutes to 4 hours.

10. The method of claim 1, wherein the slurry is first heated to a temperature of 30° C. to 80° C., maintained at 30° C. to 80° C. until the pH is below 9, then cooled to a temperature of 0° C. to 40° C.

11. The method of claim 1, wherein the slurry is first heated to a temperature of 50° C. to 80° C., maintained at 50° C. to 80° C. until the pH is below 9, then cooled to a temperature of 0° C. to 25° C.

12. The method of claim 1, wherein the pH of the starting slurry is 10 to 14.

13. The method of claim 1, wherein the slurry with arginine content greater than 65% by weight is contacted with carbon dioxide until the slurry has a pH below 8.5.

14. The method of claim 1, wherein the arginine bicarbonate is recovered from the slurry by evaporation or precipitation.

15. The method of claim 1, comprising additionally adding sodium bicarbonate to the slurry.

16. A process for producing arginine bicarbonate comprising:
contacting an arginine water slurry with carbon dioxide having a pressure greater than 551580 Pa (80 psi);
heating the arginine water slurry to a temperature of 60° C. to 80° C.;
adding arginine to the slurry until arginine comprises 65% by weight;
contacting carbon dioxide with the increased arginine slurry until the slurry has a pH below 9;
cooling the slurry to a temperature of 25° C.

17. A method of producing arginine bicarbonate comprising:
subjecting an arginine water slurry to elevated pressure and temperature;
contacting the slurry with carbon dioxide to form a slurry comprising arginine and bicarbonate in excess of 65% by weight of arginine; and
recovering arginine bicarbonate from the slurry,
wherein arginine is added to the contacted slurry continuously in the form of a free base or a salt.

18. The method of claim 17 wherein the slurry comprises water.

* * * * *